United States Patent
Pado (10) Patent No.: US 7,734,429 B2
(45) Date of Patent: Jun. 8, 2010

(54) METHOD AND APPARATUS FOR CREATING AT LEAST ONE PARAMETER FOR ALGORITHMICALLY EVALUATING DAMAGE IN A STRUCTURE

(75) Inventor: Lawrence E. Pado, Saint Charles, MO (US)

(73) Assignee: Boeing Company, Chicago, IL (US)

( * ) Notice: Subject to any disclaimer, the term of this patent is extended or adjusted under 35 U.S.C. 154(b) by 329 days.

(21) Appl. No.: 11/872,335

(22) Filed: Oct. 15, 2007

(65) Prior Publication Data
US 2009/0099790 A1   Apr. 16, 2009

(51) Int. Cl.
*G01B 5/28* (2006.01)

(52) U.S. Cl. ............................. 702/35; 73/579; 73/587; 702/34; 702/36

(58) Field of Classification Search ............. 702/33–36, 702/39, 42, 43, 75–77, 103, 116, 124, 171, 702/179, 183–185; 73/579, 583; 156/58; 703/1, 7
See application file for complete search history.

(56) References Cited

U.S. PATENT DOCUMENTS

| | | | | |
|---|---|---|---|---|
| 4,061,017 A | * | 12/1977 | Sloane et al. | ............. 73/579 |
| 5,195,046 A | * | 3/1993 | Gerardi et al. | ............. 702/35 |
| 5,327,358 A | * | 7/1994 | Stubbs | ............. 702/36 |
| 5,665,913 A | * | 9/1997 | Chung | ............. 73/583 |
| 6,006,163 A | * | 12/1999 | Lichtenwalner et al. | ....... 702/36 |
| 7,426,447 B2 | | 9/2008 | Pado | |

OTHER PUBLICATIONS

Bovio and Lecce; "Health Monitoring: New Techniques Based on Vibrations Measurements and Identification Algorithms"; Department of Aeronautical Engineering, University of Naples; Naples, Italy; Jan. 14, 2005.

* cited by examiner

*Primary Examiner*—John H Le
(74) *Attorney, Agent, or Firm*—Law Office of Donald D. Mondul (57) ABSTRACT

A method for creating at least one input parameter for an algorithmic system to evaluate damage in a structure may include: (a) Determining a plurality of damage index factors using first signal information relating to a first signal transmitted through the structure before the damage is imposed, and second signal information relating to a second signal transmitted through the structure after the damage is imposed. (b) determining a plurality of condensed damage index factors using the plurality of damage index factors. (c) Correlating selected of the condensed damage index factors with selected measured dimensions relating to the damage to determine a correlation index for selected combinations of the condensed damage index factors and the dimensions. (d) Selecting the at least one input parameter from among the selected condensed damage index factors having a correlation index meeting at least one predetermined criterion.

20 Claims, 6 Drawing Sheets

| | MAX DI | AVG DI | MAX DECOMP | RMS ΔDI MEAN - 3" | RMS ΔDI WEIGHTED MEAN - 3" | RMS ΔDI MAX - 3" | RMS ΔDI WEIGHTED MAX - 3" |
|---|---|---|---|---|---|---|---|
| 61 MAX DI | 1.00 | | | | | | |
| 62 AVG DI | 0.63 | 1.00 | | | | | |
| 63 MAX DECOMP | 0.42 | 0.31 | 1.00 | | | | |
| 64 RMS ΔDI MEAN - 3" | 0.80 | 0.36 | 0.40 | 1.00 | | | |
| 65 RMS ΔDI WEIGHTED MEAN - 3" | 0.55 | 0.10 | 0.19 | 0.58 | 1.00 | | |
| 66 RMS ΔDI MAX - 3" | 0.62 | 0.19 | 0.07 | 0.70 | 0.40 | 1.00 | |
| 67 RMS ΔDI WEIGHTED MAX - 3" | 0.59 | 0.18 | 0.07 | 0.61 | 0.94 | 0.55 | 1.00 |
| 70 VOL UNDAMAGED | 0.48 | 0.19 | 0.69 | 0.60 | 0.54 | 0.20 | 0.35 |
| 71 VOL DELAM | 0.51 | 0.19 | 0.57 | 0.62 | 0.67 | 0.20 | 0.49 |
| 72 VOL NONDELAM | 0.42 | 0.17 | 0.74 | 0.55 | 0.40 | 0.18 | 0.21 |
| 73 AREA | 0.54 | 0.30 | 0.55 | 0.69 | 0.63 | 0.22 | 0.49 |
| 74 DEPTH MAX | 0.07 | -0.04 | 0.63 | 0.25 | 0.20 | 0.01 | 0.04 |
| 75 DEPTH AVG | 0.41 | 0.10 | 0.68 | 0.61 | 0.29 | 0.19 | 0.16 |
| 76 CIRCUM | 0.55 | 0.33 | 0.41 | 0.70 | 0.69 | 0.26 | 0.57 |
| 77 DELAM PERCENT | 0.26 | 0.28 | -0.50 | 0.24 | 0.19 | 0.19 | 0.25 |

METHOD AND APPARATUS FOR CREATING AT LEAST ONE PARAMETER FOR ALGORITHMICALLY EVALUATING DAMAGE IN A STRUCTURE

FIELD

The present is directed to Structural Health Monitoring (SHM) methods and systems, and especially to methods and systems for algorithmically evaluating damage in structures.

BACKGROUND

A Structural Health Monitoring (SHM) system may improve unscheduled and scheduled maintenance operations. An SHM system may advantageously quickly identify occurrence of damage, determine damage location and size, and schedule an appropriate remedial maintenance action. Such an SHM system may reduce maintenance costs.

An SHM system may be employed with an aircraft, by way of example and not by way of limitation, using a plurality of transducers in a transducer array coupled with a structure, such as near the fuselage cargo door of an aircraft where baggage handlers may collide with and cause impact damage to the airplane fuselage, may reduce aircraft schedule cancellations and delays. An SHM system may be particularly advantageous when employed in connection with laminated structures to identify, locate and characterize delamination damage.

An exemplary algorithmic tool for use in evaluating damage to a structure may be an artificial neural network. Neural Networks (NN) may be described as nonlinear algorithms that learn by example. Generally speaking, the smaller the dimension of a training record provided to a NN to effect the learning process by the NN, the fewer records that may be needed for training and the better the NN may be relied upon for generalized conclusions in evaluating real damage to a structure.

For SHM preparation by training an NN, each impact to a structure may produce one training record. Generating more than a few hundred impacts (and thus a few hundred training records) and measuring the response of the transducer array to each impact may be cost prohibitive. If a low number of training records is employed, it may be advisable to provide a limited relatively small number of input factors to an NN associated with an SHM to better assure reliable results.

There is a need for a method and apparatus for creating at least one parameter for algorithmically evaluating damage in a structure that may facilitate accurate evaluation.

SUMMARY

A method for creating at least one input parameter for an algorithmic system to evaluate damage in a structure may include: (a) Determining a plurality of damage index factors using first signal information relating to a first signal transmitted through the structure before the damage is imposed, and second signal information relating to a second signal transmitted through the structure after the damage is imposed. (b) determining a plurality of condensed damage index factors using the plurality of damage index factors. (c) Correlating selected of the condensed damage index factors with selected measured dimensions relating to the damage to determine a correlation index for selected combinations of the condensed damage index factors and the dimensions. (d) Selecting the at least one input parameter from among the selected condensed damage index factors having a correlation index meeting at least one predetermined criterion.

An apparatus for selecting at least one input parameter for an algorithmic system to assess damage in a structure may include: (a) at least one first signal transmitting unit coupled with the structure; (b) at least one first signal receiving unit coupled with the structure; the at least one first transmitting unit transmitting at least one first signal traversing the structure from the at least one first transmitting unit to the at least one first receiving unit through a first target area; (c) a first data storing unit coupled with at least one selected first signal receiving unit; the first data storing unit storing first signal information relating to the at least one first signal; (d) at least one second signal transmitting unit coupled with the structure; (e) at least one second signal receiving unit coupled with the structure; the at least one second transmitting unit transmitting at least one second signal traversing the structure from the at least one second transmitting unit to the at least one second receiving unit through a second target area; (f) a second data storing unit coupled with at least one selected second signal receiving unit of the at least one second signal receiving unit; the second data storing unit storing second signal information relating to the at least one second signal after damage has been imposed to the structure; at least a portion of the damage being substantially situated within the target area; (g) a first processing unit coupled with the first data storing unit and the second data storing unit; the first processing unit determining a plurality of condensed damage index factors using the stored first signal information and the stored second signal information; (h) a second processing unit coupled with the first processing unit; the second processing unit determining a plurality of condensed damage index factors using at least one damage index factor of the plurality of damage index factors; (i) a correlating unit coupled with the processing unit; the correlating unit effecting correlation of selected condensed damage index factors of the plurality of condensed damage index factors with selected measured dimensions of the damage to determine a correlation index for selected combinations of the selected condensed damage index factors and the selected measured dimensions; and (j) a selecting unit coupled with the correlating unit; the selecting unit effecting selection of the at least one input parameter from among the selected condensed damage index factors having a correlation index meeting at least one predetermined criterion.

It is, therefore, a feature of embodiments of the present disclosure to provide a method and apparatus for creating at least one parameter for algorithmically evaluating damage in a structure that may facilitate accurate evaluation.

Further features of the present disclosure will be apparent from the following specification and claims when considered in connection with the accompanying drawings, in which like elements are labeled using like reference numerals in the various figures, illustrating embodiments of the disclosure.

DETAILED DESCRIPTION

One example of an algorithmic system suitable for use in evaluating signals from a transducer array, such as by way of example and not by way of limitation in a Structural Health Monitoring (SHM) system, may be an artificial Neural Network (NN). However in order for a NN to generalize a data space and accurately perform, it may be preferred that a small number of inputs be included in each input set. Too large a number of inputs may cause a neural network to be unable to generalize using new input sets and the network may thereby be rendered incapable of accurately predicting damage of a large range of possible sizes.

Figure 1:
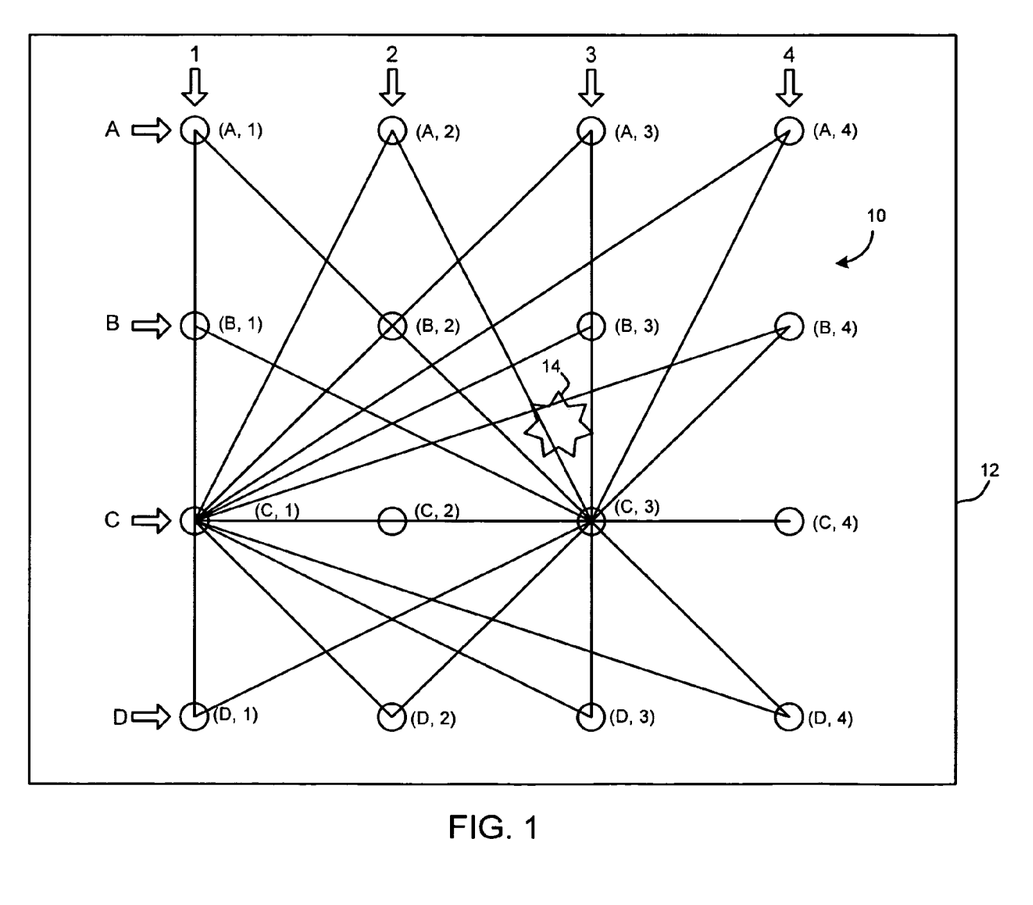
FIG. 1 is a schematic illustration of a transducer array useful in effecting embodiments of the present disclosure.

FIG. 1 is a schematic illustration of a transducer array useful in effecting embodiments of the present disclosure. In FIG. 1, an array of transducer elements 10 may be affixed or coupled to a structure 12. Array 10 may present an arrangement of transducer elements in any pattern. An exemplary pattern may be a rectangular grid having rows A, B, C, D and columns 1, 2, 3, 4, as illustrated in FIG. 1. Alternatively, every other row may be offset from the row above it so that each transducer may be substantially half way between transducers in rows above and below. In FIG. 1, individual transducer elements may be identified using (row, column) coordinates. Thus, column 1 may contain a transducer element (A,1) in row A, a transducer element (B,1) in row B, a transducer element (C,1) in row C and a transducer element (D,1) in row D. Column 2 may contain a transducer element (A,2) in row A, a transducer element (B,2) in row B, a transducer element (C,2) in row C and a transducer element (D,2) in row D. Column 3 may contain a transducer element (A,3) in row A, a transducer element (B,3) in row B, a transducer element (C,3) in row C and a transducer element (D,3) in row D. Column 4 may contain a transducer element (A,4) in row A, a transducer element (B,4) in row B, a transducer element (C,4) in row C and a transducer element (D,4) in row D. Array 10 is exemplary only. An array of transducer elements may contain a greater number of transducer elements if desired.

During training or evaluation of damage operations each respective transducer element may be excited to transmit a signal which may be received by some or all of the remaining non-transmitting transducer elements. A signal path may be thereby between each transmitting-receiving transducer-pair. One may excite each transducer individually for presenting a respective signal for receiving by non-transmitting transducer elements to establish a plurality of signal paths traversing the array 10 of transducer elements.

One may observe that there may be presented a total of 240 (16×15) signal paths in array 10 after all 16 transducer elements have had a turn at transmitting. In order to avoid a cluttered and confusing presentation, FIG. 1 illustrates only two representative transmitting transducer elements (C,1), (C,3). One of transducer elements (C,1), (C,3) may transmit first along a first set of 15 signal paths for receiving by other then-non-transmitting transducer elements in array 10. Subsequently, an other transducer of transducer elements (C,1), (C,3) may transmit along a second set of 15 signal paths for receiving by other then-non-transmitting transducer elements in array 10. A damage locus 14 is also indicated in FIG. 1. One may also observe that selected signal paths presented in array 10 may pass near damage locus 14 or traverse damage locus 14. Structural changes may occur in structure 12 as a result of damage situated at damage locus 14, and such structural changes may alter selected characteristics of signals traversing signal paths in the vicinity of damage locus 14 or traversing damage locus 14.

An algorithmic system may be trained to associate observed anomalies in signals received by receiving transducer elements with selected physical manifestations of damage. The training process may involve transmitting signals through structure 12 from all transducer elements in array 10 and recording signal characteristics of signals received by receiving transducer elements when there is no damage to structure 12. Thereafter in a training process, some damage may be imposed upon structure 12, signals may again be transmitted through structure 12 from all transducer elements in array 10 and post-damage signal characteristics of signals received by receiving transducer elements may be recorded or stored. Measuring predetermined characteristics of the imposed damage may permit recognition of an association with the measured parameters and the changes in received signals traversing selected signal paths. Measurement of characteristic relating to a damage locus may be effected using one or more known measurement techniques such as, by way of example and not by way of limitation, physical measurement using calipers, dividers, distance scales and similar instruments; x-ray measurements, ultrasonic measurements and other known measurement techniques.

A training operation may further involve repeating the above-described process using a plurality of training pieces in order to refine associations observed between measured parameters of damage loci and changes in received signal characteristics.

Once the algorithmic system is trained, it may be substantially copied to present a trained algorithmic system that may be employed to evaluate a test piece. Signals may be transmitted through the test piece substantially as signals were transmitted through one or more training pieces and characteristics of signals received by receiving transducer elements may be evaluated. If the signals evaluated exhibit little or no change (i.e., below a predetermined threshold of change) from transmitted signals, one may conclude that the test piece is undamaged. If signals evaluated exhibit sufficient change (i.e., above a predetermined threshold of change), there may be damage to the test piece. The nature of the observed signal changes may be employed to estimate predetermined aspects of the damage based upon the correlations between signal changes and damage parameters "learned" by the algorithmic system during the training operation.

Figure 2:
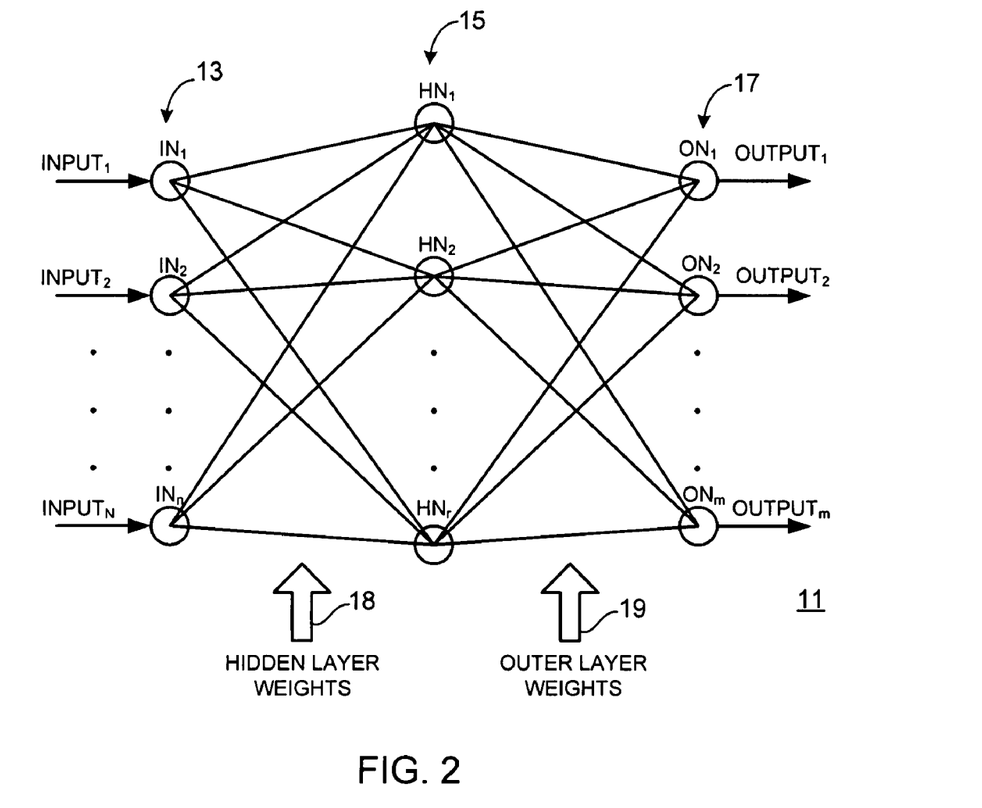
FIG. 2 is a schematic illustration of an artificial neural network that may be useful in effecting embodiments of the present disclosure.

One example of an algorithmic system suitable for use in evaluating signals from array 10, such as by way of example and not by way of limitation in a Structural Health Monitoring (SHM) system, may be an artificial neural network. However in order for a neural network to generalize a data space and accurately perform, it may be preferred that a small number of inputs be included in each input set. Too large a number of inputs may cause a neural network to be unable to generalize using new input sets and the network may thereby be rendered incapable of accurately predicting damage of a large range of possible sizes. FIG. 2 is a schematic illustration of an artificial neural network that may be useful in effecting embodiments of the present disclosure. In FIG. 2, an artificial Neural Network (NN) 11 may include a plurality of input nodes $IN_1$, $IN_2$, $IN_n$. The indicator "n" is employed to signify that there can be any number of input nodes in NN 11. The inclusion of three input nodes $IN_1$, $IN_2$, $IN_n$ in FIG. 2 is illustrative only and does not constitute any limitation regarding the number of input nodes that may be included in an NN that may be employed with the present disclosure. Input nodes $IN_n$ may receive input factors so that input node $IN_1$ may receive an input factor $INPUT_1$, input node $IN_2$ may receive an input factor $INPUT_2$ and input node $IN_n$ may receive an input factor $INPUT_n$.

NN 11 may also include a plurality of output nodes $ON_1$, $ON_2$, $ON_m$. The indicator "m" is employed to signify that there can be any number of output nodes in NN 11. The inclusion of three output nodes $ON_1$, $ON_2$, $ON_m$ in FIG. 2 is illustrative only and does not constitute any limitation regarding the number of output nodes that may be included in an NN that may be employed with the present disclosure. Output nodes $ON_n$ may present output factors so that output node $IN_1$ may present an output factor $OUTPUT_1$, output node $ON_2$ may present an output factor $OUTPUT_2$ and output node $ON_m$ may present an output factor $OUTPUT_m$.

NN 11 may also include a plurality of hidden nodes $HN_1$, $HN_2$, $HN_r$ situated between input nodes $IN_n$ and output nodes $ON_m$. The indicator "r" is employed to signify that there can be any number of hidden nodes in NN 11. The inclusion of three hidden nodes $HN_1$, $HN_2$, $HN_r$ in FIG. 2 is illustrative only and does not constitute any limitation regarding the number of hidden nodes that may be included in an NN that may be employed with the present disclosure. Only one "tier" of hidden nodes $HN_r$ is illustrated in FIG. 2. NN 11 may include more than one tier of hidden nodes $HN_r$.

Hidden layer weights may be applied to selected signals traversing signal paths between particular input nodes $IN_n$ and particular hidden nodes $HN_r$, as indicated by an arrow 18. Some paths between particular input nodes $IN_n$ and particular hidden nodes $HN_r$ may be embodied in feedback paths (not illustrated in FIG. 2). Hidden layer weights may be applied, by way of example and not by way of limitation, as weighted factors applied to signals traversing signal paths between particular input nodes $IN_n$ and particular hidden nodes $HN_r$.

Outer layer weights may be applied to selected signals traversing signal paths between particular hidden nodes $HN_r$ and particular output nodes $ON_m$ as indicated by an arrow 19. Some paths between particular hidden nodes $HN_r$ and particular output nodes $ON_m$ may be embodied in feedback paths (not illustrated in FIG. 2). Outer layer weights may be applied, by way of example and not by way of limitation, as weighted factors applied to signals traversing signal paths between particular hidden nodes $HN_r$ and particular output nodes $ON_m$.

During training or evaluation of damage operations each respective transducer element of an array of transducers coupled or bonded with a structure may be excited to transmit a signal which may be received by some or all of the remaining non-transmitting transducer elements in the transducer array. A signal path may be thereby established between each transmitting-receiving transducer-pair. One may excite each transducer individually for presenting a respective signal for receiving by non-transmitting transducer elements to establish a plurality of signal paths traversing the array of transducer elements.

Figure 3:
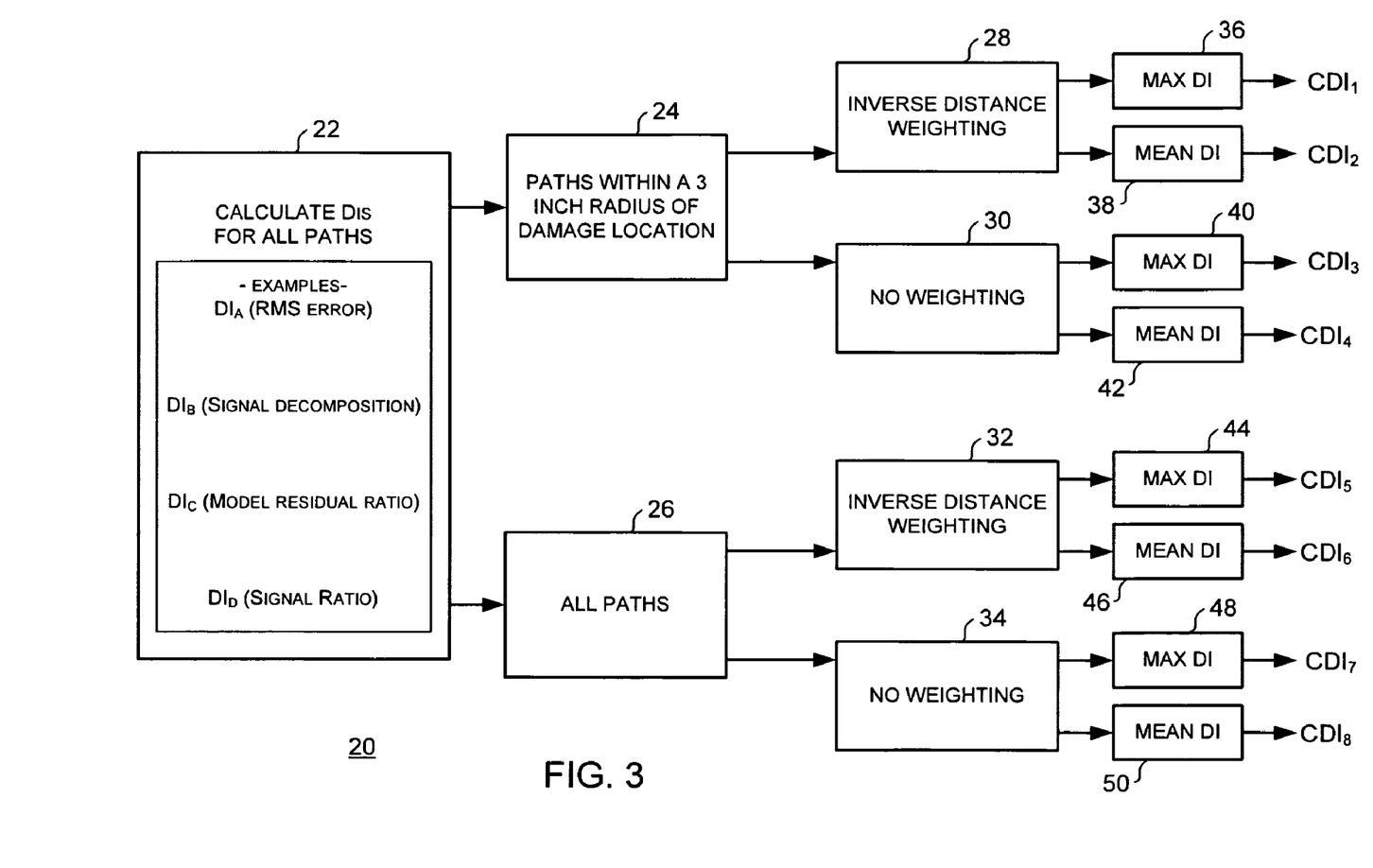
FIG. 3 is a schematic exemplary illustration of an embodiment of a process for determining condensed damage index factors.

FIG. 3 is a schematic exemplary illustration of an embodiment of a process for determining condensed damage index factors. Determining condensed damage index factors may be an interim step in selecting parameters for algorithmically evaluating damage in a structure. In FIG. 3, a process 20 begins with calculating damage index (DI) factors for all signal paths using a plurality of DI calculating methods, as indicated by a block 22. By way of example and not by way of limitation, four different damage index factors are calculated in block 22: $DI_A$, $DI_B$, $DI_C$, $DI_D$. By way of further example and not by way of limitation, using transducer element array 10 (FIG. 1), calculating four damage index factors may yield as many as 960 [240×4] damage index factors for the 240 paths possible with 16 transducer elements. Damage index factor calculations may involve comparison of before-damage signals with after-damage signals in training structures subjected to intentional damage. Aspects of damage loci may be measured and correlations between measured aspects of damage loci and damage index factors or other signal characteristics may be observed. By way of further example and not by way of limitation, damage index factor $DI_A$ may be calculated employing a RMS (Root Mean Square Error) technique. Damage index factor $DI_B$ may be calculated employing a signal decomposition technique. Damage index factor $DI_C$ may be calculated employing a model residual ratio technique. Damage index factor $DI_D$ may be calculated employing a signal ratio technique.

Process 20 may proceed by selecting each of the calculated damage index factors $DI_A$, $DI_B$, $DI_C$, $DI_D$ calculated using paths within a predetermined radius of the locus of extant damage in the training structure, such as by way of example and not by way of limitation, three inches, as indicated by a block 24.

In order to avoid presenting a confusing and cluttered figure, each arrow connecting blocks in FIG. 3 indicates calculations relating to one respective DI factor. Treatments in various blocks in FIG. 3 involving the various DI factors $DI_A$, $DI_B$, $DI_C$, $DI_D$ may be carried out in parallel, in serial fashion, interleavedly (i.e., individually treating DI factors at each block-stage in no particular order) or in another manner without departing from the spirit of embodiments of the disclosure. Serial individual treatment of DI factors among various blocks in FIG. 3 will be described in order to straightforwardly describe process 20.

Process 20 may also proceed by taking each of the calculated damage index factors $DI_A$, $DI_B$, $DI_C$, $DI_D$ calculated using all paths among transducer elements in the transducer array coupled with the training structure, as indicated by a block 26.

Weighting of signal factors during algorithmic treatment may be effected for results presented by block 24, as indicated by a block 28. By way of example and not by way of limitation, weighting may be based upon inverse distance of a respective path from center of the extant damage locus. An alternate treatment of results presented by block 24 may be to apply no weighting, as indicated by a block 30.

Weighting of signal factors during algorithmic treatment may be effected for results presented by block 26, as indicated by a block 32. By way of example and not by way of limitation, weighting may be based upon inverse distance of a respective path from center of the extant damage locus. An alternate treatment of results presented by block 26 may be to apply no weighting, as indicated by a block 34.

A maximum DI value among DI factor results presented by block 28 may be selected as a first condensed DI factor $CDI_1$ presented by a block 36. A mean value DI factor of DI factor results presented by block 28 may be selected as a second condensed DI factor $CDI_2$ presented by a block 38.

A maximum DI value among DI factor results presented by block 30 may be selected as a third condensed DI factor $CDI_3$ presented by a block 40. A mean value DI factor of DI factor results presented by block 30 may be selected as a fourth condensed DI factor $CDI_4$ presented by a block 42.

A maximum DI value among DI factor results presented by block 32 may be selected as a fifth condensed DI factor $CDI_5$ presented by a block 44. A mean value DI factor of DI factor results presented by block 32 may be selected as a sixth condensed DI factor $CDI_6$ presented by a block 46.

A maximum DI value among DI factor results presented by block 34 may be selected as a seventh condensed DI factor $CDI_7$ presented by a block 48. A mean value DI factor of DI factor results presented by block 34 may be selected as an eighth condensed DI factor $CDI_8$ presented by a block 50.

Other criteria may be employed for creating condensed DI factors. Alternatively, additional criteria may be employed for creating additional condensed DI factors. The point may be to pare down the mass of data presented by calculations performed by block 22—DI factors for each signal path for each of four DI factor calculation techniques $DI_A$, $DI_B$, $DI_C$, $DI_D$. By way of example and not by way of limitation, if one employs an array of 16 transducer element and each transducer element in the array has a turn sending a signal received by the remaining 15 transducer elements, there may be 240 (16×15) signal paths in the array. If each signal includes 1024 recorded data points, each DI factor calculation will present 245,760 (240×1024) data points. Using four DI factor calculation techniques $DI_A$, $DI_B$, $DI_C$, $DI_D$, one may present 983,040 data points from block 22. Such a large number of inputs may overwhelm an algorithm used to evaluate damage in a test structure. Such a large number of inputs may have a significantly deleterious effect on an artificial Neural Network (NN). By applying sorting and condensing criteria, such as criteria represented by blocks 24-50, one may select, create or identify a small number of input parameters that may permit more efficient and timelier employment of an algorithm for evaluation of damage. In a preferred embodiment of employment of the present disclosure, one may select, create or identify a single input parameter for use with an algorithm, such as an artificial neural network algorithm, for evaluation of damage.

One may wish to keep in mind that condensed damage index factors CDI1-CDI8 represent CDI factors developed using only one of damage indexes $DI_A$, $DI_B$, $DI_C$, $DI_D$. That is, process 20 actually presents a total of 32 (4×8) condensed damage index factors. It may be advantageous to reduce input factors or parameters for an algorithm, such as an N network, to a lesser number than 32.

Figure 4:
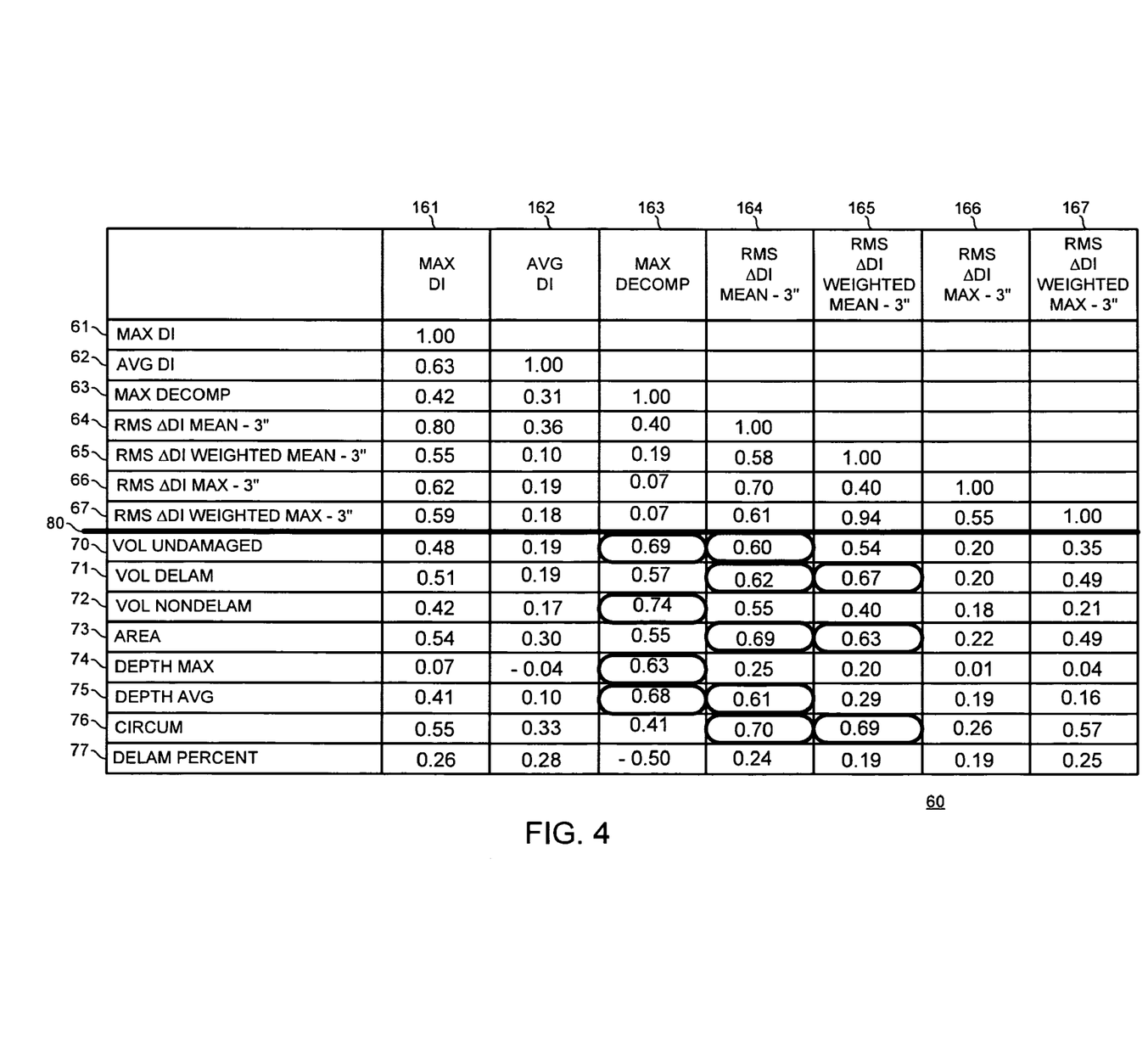
FIG. 4 is an exemplary illustration of a process for selecting input parameters from among condensed damage index factors.

FIG. 4 is an exemplary illustration of a process for selecting input parameters from among condensed damage index factors. In FIG. 4, a chart 60 tabulates linear correlation results for selected representative condensed DI (CDI) factors vis-a-vis the selected representative CDI factors in rows above a heavy horizontal line 80. Chart 60 also tabulates linear correlation results for selected measured aspects of a damage locus (i.e., Damage Aspects) vis-a-vis the selected representative CDI factors in rows below horizontal line 80.

CDI factor MAX DI may be found at row 61. CDI factor MAX DI may be the maximum CDI value obtained from all CDI factor calculations associated with FIG. 3. Recall that FIG. 3 ultimately reflects presentation of a representative 32 CDI factors.

CDI factor AVG DI may be found at row 62. CDI factor AVG DI may be the maximum CDI value obtained from all CDI factor calculations associated with FIG. 3.

CDI factor MAX DECOMP may be found at row 63. CDI factor MAX DECOMP may be the CDI factor resulting from calculation of DI factor $DI_B$ (Signal Decomposition) and presented at block 48 [All Paths; No Weighting; MAX DI].

CID factor RMS ΔDI MEAN—3" may be found at row 64. CDI factor RMS ΔDI MEAN—3" may be the CDI factor resulting from calculation of DI factor $DI_A$ (RMS Error) and presented at block 42 [3" Radius Paths; No Weighting; MEAN DI].

CDI factor to RMS ΔDI WEIGHTED MEAN—3" may be found at row 65. CDI factor to RMS ΔDI WEIGHTED MEAN—3" may be the CDI factor resulting from calculation of DI factor $DI_A$ (RMS Error) and presented at block 38 [3" Radius Paths; With Weighting; MEAN DI].

CDI factor RMS ΔDI MAX—3" may be found at row 66. CDI factor RMS ΔDI MAX—3" may be the CDI factor resulting from calculation of DI factor $DI_A$ (RMS Error) and presented at block 40 [3" Radius Paths; No Weighting; MAX DI].

CDI factor RMS ΔDI WEIGHTED MAX—3" may be found at row 67. CDI factor RMS ΔDI WEIGHTED MAX—3" may be the CDI factor resulting from calculation of DI factor $DI_A$ (RMS Error) and presented at block 36 [3" Radius Paths; With Weighting; MAX DI].

Damage Aspect VOL UNDAMAGED may be found at row 70. Damage aspect VOL UNDAMAGED may be related with volume of a structure before damage occurs to the structure.

Damage Aspect VOL DELAM may be found at row 71. Damage aspect VOL DELAM may be related with volume of a laminated structure after damage occurs to the structure that causes delamination.

Damage Aspect VOL NONDELAM may be found at row 72. Damage Aspect VOL NONDELAM may be related with volume of a laminated structure before damage occurs to the structure causing delamination.

Damage Aspect AREA may be found at row 73. Damage Aspect AREA may be related with area of a damage locus in a structure.

Damage Aspect DEPTH MAX may be found at row 74. Damage Aspect DEPTH MAX may be related with the maximum depth of a damage locus in a structure.

Damage Aspect DEPTH AVG may be found at row 75. Damage Aspect DEPTH AVG may be related with the average depth of a damage locus in a structure.

Damage Aspect CIRCUM may be found at row 76. Damage Aspect CIRCUM may be related with the circumference of a damage locus in a structure.

Damage Aspect DELAM PERCENT may be found at row 77. Damage Aspect DELAM PERCENT may be related with percentage of delamination present within a damage locus.

The selected representative CDI factors correlated are arrayed in columns: Column 161 contains correlations with respect to MAX DI; column 162 contains correlations with respect to AVG DI; column 163 contains correlations with respect to is MAX DECOMP; column 164 contains correlations with respect to RMS ΔDI MEAN—3"; column 165 contains correlations with respect to RMS ΔDI WEIGHTED MEAN—3"; column 166 contains correlations with respect to RMS ΔDI MAX—3"; column 167 contains correlations with respect to RMS ΔDI WEIGHTED MAX—3".

Figures tabulated at respective row-column intersections indicate linear correlation of the row factor—column factor of the respective intersection. One may regard a correlation of 0.60 as a measure of acceptable correlation that may be a basis for selecting a parameter for use in an algorithm for evaluating damager in a structure, such as in connection with a Structural Health Monitoring (SHM) system.

Occurrences of correlation equal with 0.60 or greater in chart 60 have been indicated by a heavy circle notation. Column 163 presents correlations greater than or equal to 0.60 at rows 70, 72, 74, 75. Column 164 presents correlations greater than or equal to 0.60 at rows 70, 71, 73, 75, 76. Column 165 presents correlations greater than or equal to 0.60 at rows 71, 73, 76.

The higher incidences of correlation equal to or greater than 0.60 in columns 163, 164 indicate selection of CDI factors MAX DECOMP and RMS ΔDI MEAN—3" as parameters for use in an algorithm for evaluating damage in the structure, such as by using an NN network.

Figure 5:
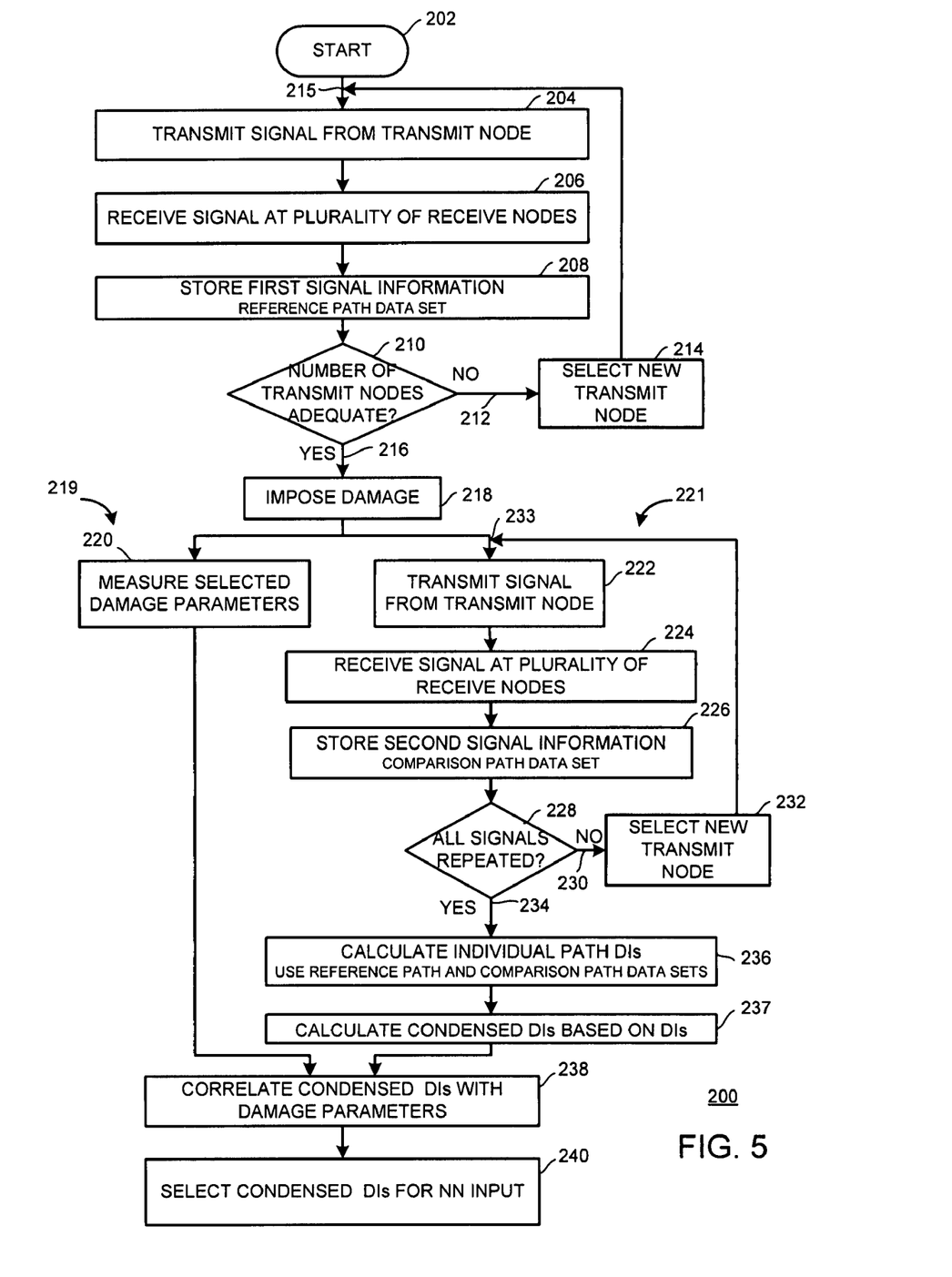
FIG. 5 is a flow chart illustrating an embodiment of the method of the disclosure.

FIG. 5 is a flow chart illustrating an embodiment of the method of the disclosure. In FIG. 5, a method 200 for selecting at least one parameter for algorithmically evaluating damage in a structure may begin at a START locus 202. Method 200 may continue by transmitting a signal from a transmit node through a training structure, such as from a selected transducer elements among an array of transducer elements coupled with the training structure (see FIG. 1), as indicated by a block 204.

Method 200 may continue with receiving the transmitted signal at a plurality of receive nodes, such as non-transmitting transducer elements in an array of transducer elements (see FIG. 1), as indicated by a block 206. Method 200 may continue by storing first signal information relating to signals received by the plurality of receive nodes, as indicated by a block 208. The first signal information stored may be referred to as a reference path data set.

Method 200 may continue by posing a query whether the number of transmit nodes for which first signal information has been stored is adequate for accurate damage analysis, as indicated by a query block 210. If the number of transmit nodes for which first signal information has been stored is not adequate for accurate damage analysis, method 200 proceeds from query block 210 via a NO response line 212 and a new transmit node is selected, as indicated by a block 214. Method 200 thereafter proceeds to a locus 215 and method steps indicated by blocks 204, 206, 208, 210 may be repeated.

If the number of transmit nodes for which first signal information has been stored is adequate for accurate damage analysis, method 200 proceeds from query block 210 via a YES response line 216 and damage may be imposed upon the training structure, as indicated by a block 218.

Method 200 may continue in two parallel method sequences 219, 221 in no particular order. Method sequence 219 may proceed from block 218 to effect measuring of selected parameters associated with the imposed damage, as indicated by a block 220.

Method sequence 221 may proceed from block 218 by transmitting a signal from a transmit node through a training structure, such as from selected transducer elements among an array of transducer elements coupled with the now-damaged training structure, as indicated by a block 222.

Method 200 may continue with receiving the transmitted signal at a plurality of receive nodes, such as non-transmitting transducer elements in an array of transducer elements (see FIG. 1), as indicated by a block 224. Method 200 may continue by storing second signal information relating to signals received by the plurality of receive nodes, as indicated by a block 226. The second signal information stored may be referred to as a comparison path data set.

Method 200 may continue by posing a query whether substantially all signals transmitted in connection with block 204 have been repeated, as indicated by a query block 228. If substantially all signals transmitted in connection with block 204 have not been repeated, method 200 proceeds from query block 228 via a NO response line 230 and a new transmit node is selected, as indicated by a block 232. Method 200 thereafter proceeds to a locus 233 and method steps indicated by blocks 222, 224, 226, 228 may be repeated.

If substantially all signals transmitted in connection with block 204 have been repeated, method 200 may proceed from query block 228 via a YES response line 234 and Damage Indexes (DIs) may be calculated using the reference path data set (block 208) and the comparison path data set (block 226), as indicated by a block 236.

Method 200 may continue with calculating Condensed Damage Indexes (CDIs) based on DIs calculated pursuant to block 236, as indicated by a block 237.

At this juncture of method 200, method sequences 219, 221 may merge and method 200 may continue by correlating CDIs (calculated pursuant to block 237) with damage parameters (measured pursuant to block 220), as indicated by a block 238.

Method 200 may continue with selecting at least one Condensed DI (i.e., CDI) for employment as at least one parameter for algorithmically evaluating damage in a structure, as indicated by a block 240. It is preferred that few CDIs are selected pursuant to block 240. It is especially preferred that one CDI be selected pursuant to block 240.

Figure 6:
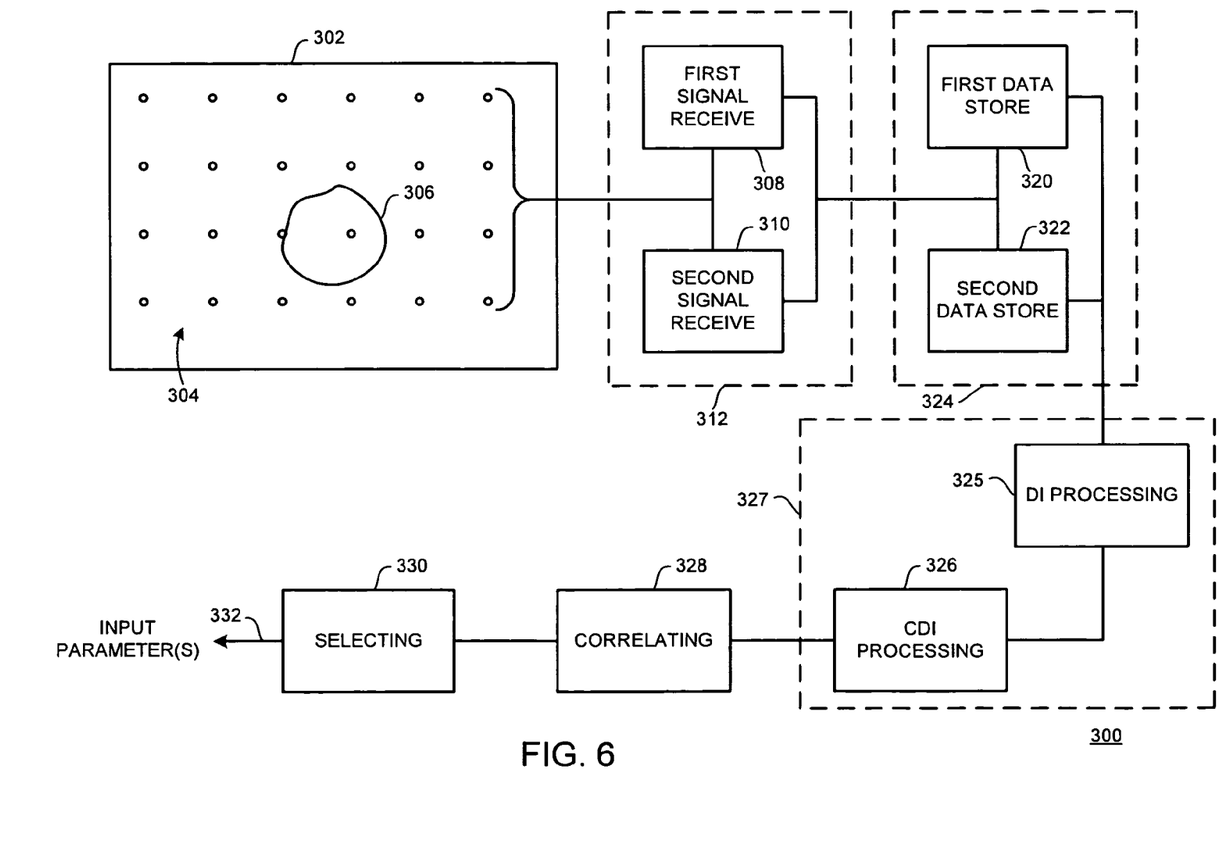
FIG. 6 is a schematic illustration of an embodiment of the apparatus of the disclosure.

FIG. 6 is a schematic illustration of an embodiment of the apparatus of the disclosure. In FIG. 6, an apparatus 300 for selecting at least one input parameter for an algorithmic system to assess damage in a structure 302 may include an array of signal transducer elements 304 coupled with structure 302. Each of the respective transducer elements in array 304 may operate individually as a transmitting element to transmit a signal through structure 302 for receiving by at least one first signal receiving unit 308. The at least one first signal receiving unit 308 may be embodied in other non-transmitting transducer elements of array 304 than the transmitting transducer element. Signals transmitted may be ultrasonic signals, such as lamb waves, and some signals may traverse a first target area 306 in structure 302. Coupling of individual transducer elements in array 304 with first signal receiving unit 308 is indicated generally by a bracket notation so as not to present a cluttered confusing figure.

Lamb waves may be ultrasonic waves similar to longitudinal waves, exhibiting compression and rarefaction. However, lamb waves may be bounded by a sheet or plate surface causing a wave-guide effect in a structure through which the lamb waves may be transmitted.

A first data storing unit 320 may be coupled with at least one selected first signal receiving unit of the at least one first signal receiving unit 308. The first data storing unit 320 may store first signal information relating to the at least one first signal.

At least one second signal receiving unit 310 may be coupled with structure 302. At least one second transmitting unit in array 304 may transmit at least one second signal traversing structure 304 from the at least one second transmitting unit in array 304 to the at least one second receiving unit 310 through a second target area. A separate second target area is not shown in FIG. 6; the second target area may be the same as first target area 306.

First and second at least one signal receiving units 308, 310 may be embodied in a single signal receiving unit 312.

A second data storing unit 322 may be coupled with at least one selected second signal receiving unit of the at least one second signal receiving unit 310. Second data storing unit 322 may store second signal information relating to the at least one second signal after damage has been imposed to structure 302. At least a portion of the damage may be substantially situated within target area 306. First and second data storing units 320, 322 may be embodied in a single data storing unit 324.

A Damage Index (DI) processing unit 325 may be coupled with first data storing unit 320 and second data storing unit 324. DI processing unit 325 may determine a plurality of DIs using the stored first signal information and the stored second signal information.

A Condensed Damage Index (CDI) processing unit 326 may be coupled with DI processing unit 325. CDI processing unit 326 may determine a plurality of condensed damage index factors using the DIs determined by DI processing unit 325. DI processing unit 325 and CDI processing unit 326 may be embodied in a single processing unit 327.

A correlating unit 328 may be coupled with processing unit 326. Correlating unit 328 may effect correlation of selected condensed damage index factors of the plurality of condensed damage index factors with selected measured dimensions of the damage to determine a correlation index for selected combinations of the selected condensed damage index factors and the selected measured dimensions.

A selecting unit 330 may be coupled with correlating unit 328. Selecting unit 330 may effect selection of the at least one input parameter from among the selected condensed damage index factors having a correlation index meeting at least one predetermined criterion.

It is to be understood that, while the detailed drawings and specific examples given describe embodiments of the disclosure, they are for the purpose of illustration only, that the apparatus and method of embodiments of the disclosure are not limited to the precise details and conditions disclosed and that various changes may be made therein without departing from the spirit of the disclosure which is defined by the following claims:

I claim:

1. A method for creating at least one input parameter for an algorithmic system to assess damage in a structure; the method comprising:
    (a) transmitting at least one first signal traversing said structure from at least one first transmitting unit to at least one first receiving unit through a first target area;
    (b) storing first signal information relating to said at least one first signal;
    (c) imposing damage to said structure; at least a portion of said damage being substantially situated within said first target area;
    (d) in no particular order:
        (1) measuring a plurality of dimensions relating to said damage; and
        (2) transmitting said at least one second signal traversing said structure from at least one second transmitting unit to at least one second receiving unit through a second target area; at least a portion of said damage being substantially situated within said second target area;
        (3) storing second signal information relating to said at least one second signal;
        (4) determining a plurality of damage index factors using said stored first signal information and said stored second signal information; and
        (5) determining a plurality of condensed damage index factors using at least one damage index factor of said plurality of damage index factors;
    (e) correlating selected condensed damage index factors of said plurality of condensed damage index factors with selected dimensions of said plurality of dimensions to determine a correlation index for selected combinations of said selected condensed damage index factors and said selected dimensions; and
    (f) selecting said at least one input parameter from among said selected condensed damage index factors having a correlation index meeting at least one predetermined criterion.

2. A method for creating at least one input parameter for an algorithmic system to assess damage in a structure as recited in claim 1 wherein said at least one first signal and said at least one second signal are substantially similar, and wherein said at least one first signal and said at least one second signal are each ultrasonic signals.

3. A method for creating at least one input parameter for an algorithmic system to assess damage in a structure as recited in claim 2 wherein said correlating is effected using a linear correlation technique.

4. A method for creating at least one input parameter for an algorithmic system to assess damage in a structure as recited in claim 1 wherein said at least one first transmitting unit, said at least one second transmitting unit, said at least one first receiving unit and said at least one second receiving unit are substantially the same units iteratively serving in different capacities while exercising the method.

5. A method for creating at least one input parameter for an algorithmic system to assess damage in a structure as recited in claim 4 wherein said at least one first transmitting unit, said at least one second transmitting unit, said at least one first receiving unit and said at least one second receiving unit are substantially the same units iteratively serving in different capacities while exercising the method.

6. A method for creating at least one input parameter for an algorithmic system to assess damage in a structure as recited in claim 4 wherein said correlating is effected using a linear correlation technique.

7. A method for creating at least one input parameter for an algorithmic system to assess damage in a structure as recited in claim 1 wherein said correlating is effected using a linear correlation technique.

8. A method for creating at least one input parameter for an algorithmic system to evaluate damage in a structure; the method comprising:
    (a) determining a plurality of damage index factors using first signal information and second signal information; said first signal information relating to a first signal transmitted through a target area in said structure before said damage is imposed; said second signal information relating to a second signal transmitted through said structure in said target area after said damage is imposed substantially in said target area;
    (b) determining a plurality of condensed damage index factors using said plurality of damage index factors;
    (c) correlating selected condensed damage index factors of said plurality of condensed damage index factors with selected measured dimensions relating to said damage to determine a correlation index for selected combinations of said selected condensed damage index factors and said selected dimensions; and
    (d) selecting said at least one input parameter from among said selected condensed damage index factors having a correlation index meeting at least one predetermined criterion.

9. A method for creating at least one input parameter for an algorithmic system to evaluate damage in a structure as recited in claim 8 wherein respective condensed damage index factors of said plurality of condensed damage index factors are based upon a plurality of treatments of a plurality of damage index calculations.

10. A method for creating at least one input parameter for an algorithmic system to evaluate damage in a structure as recited in claim 9 wherein said first signal and said second signal are substantially similar, and wherein said first signal and said second signal are each ultrasonic signals.

11. A method for creating at least one input parameter for an algorithmic system to evaluate damage in a structure as recited in claim 10 wherein said correlating is effected using a linear correlation technique.

12. A method for creating at least one input parameter for an algorithmic system to evaluate damage in a structure as recited in claim 9 wherein said correlating is effected using a linear correlation technique.

13. A method for creating at least one input parameter for an algorithmic system to evaluate damage in a structure as recited in claim 8 wherein said first signal and said second signal are substantially similar, and wherein said first signal and said second signal are each ultrasonic signals.

14. A method for creating at least one input parameter for an algorithmic system to evaluate damage in a structure as recited in claim 8 wherein said correlating is effected using a linear correlation technique.

15. An apparatus for creating at least one input parameter for an algorithmic system to assess damage in a structure; the apparatus comprising:
- (a) at least one first signal transmitting unit coupled with said structure;
- (b) at least one first signal receiving unit coupled with said structure; said at least one first transmitting unit transmitting at least one first signal traversing said structure from said at least one first transmitting unit to said at least one first receiving unit through a first target area;
- (c) a first data storing unit coupled with at least one selected first signal receiving unit of said at least one first signal receiving unit; said first data storing unit storing first signal information relating to said at least one first signal;
- (d) at least one second signal transmitting unit coupled with said structure;
- (e) at least one second signal receiving unit coupled with said structure; said at least one second transmitting unit transmitting at least one second signal traversing said structure from said at least one second transmitting unit to said at least one second receiving unit through a second target area;
- (f) a second data storing unit coupled with at least one selected second signal receiving unit of said at least one second signal receiving unit; said second data storing unit storing second signal information relating to said at least one second signal after damage has been imposed to said structure; at least a portion of said damage being substantially situated within said target area;
- (g) a first processing unit coupled with said first data storing unit and said second data storing unit; said first processing unit determining a plurality of damage index factors using said stored first signal information and said stored second signal information;
- (h) a second processing unit coupled with said first processing unit; said second processing unit determining a plurality of condensed damage index factors using said plurality of damage index factors;
- (i) a correlating unit coupled with said second processing unit; said correlating unit effecting correlation of selected condensed damage index factors of said plurality of condensed damage index factors with selected measured dimensions of said damage to determine a correlation index for selected combinations of said selected condensed damage index factors and said selected measured dimensions; and
- (j) a selecting unit coupled with said correlating unit; said selecting unit effecting selection of said at least one input parameter from among said selected condensed damage index factors having a correlation index meeting at least one predetermined criterion.

16. An apparatus for creating at least one input parameter for an algorithmic system to assess damage in a structure as recited in claim 15 wherein said at least one first signal and said at least one second signal are substantially similar, and wherein said at least one first signal and said at least one second signal are each ultrasonic signals.

17. An apparatus for creating at least one input parameter for an algorithmic system to assess damage in a structure as recited in claim 16 wherein said correlating is effected using a linear correlation technique.

18. An apparatus for creating at least one input parameter for an algorithmic system to assess damage in a structure as recited in claim 15 wherein said at least one first transmitting unit, said at least one second transmitting unit, said at least one first receiving unit and said at least one second receiving unit are substantially the same units iteratively serving in different capacities.

19. An apparatus for creating at least one input parameter for an algorithmic system to assess damage in a structure as recited in claim 18 wherein said at least one first transmitting unit, said at least one second transmitting unit, said at least one first receiving unit and said at least one second receiving unit are substantially the same units iteratively serving in different capacities.

20. An apparatus for creating at least one input parameter for an algorithmic system to assess damage in a structure as recited in claim 15 wherein said correlating unit effects said correlation using a linear correlation technique.

* * * * *